US009486313B2

(12) United States Patent
Stacchino et al.

(10) Patent No.: US 9,486,313 B2
(45) Date of Patent: *Nov. 8, 2016

(54) CARDIAC VALVE PROSTHESIS

(71) Applicant: Sorin Group Italia S.r.l., Milan (IT)

(72) Inventors: Carla Stacchino, Turin (IT); Giovanni Bergamasco, Turin (IT); Gaetano Burriesci, London (GB); Giovanni Righini, Gland (CH)

(73) Assignee: Sorin Group Italia S.r.l., Milan (IT)

( * ) Notice: Subject to any disclaimer, the term of this patent is extended or adjusted under 35 U.S.C. 154(b) by 37 days.

This patent is subject to a terminal disclaimer.

(21) Appl. No.: 14/548,013

(22) Filed: Nov. 19, 2014

(65) Prior Publication Data
US 2015/0148895 A1    May 28, 2015

Related U.S. Application Data

(63) Continuation of application No. 13/972,022, filed on Aug. 21, 2013, now Pat. No. 8,920,492, which is a continuation of application No. 13/341,336, filed on Dec. 30, 2011, now Pat. No. 8,540,768, which is a
(Continued)

(30) Foreign Application Priority Data

Feb. 10, 2005   (IT) ............................... TO2005A0074

(51) Int. Cl.
*A61F 2/24*  (2006.01)
*A61F 2/848* (2013.01)

(52) U.S. Cl.
CPC .......... *A61F 2/2418* (2013.01); *A61F 2/2436* (2013.01); *A61F 2/2469* (2013.01);
(Continued)

(58) Field of Classification Search
CPC ....... A61F 2/2412; A61F 2/2418; A61F 2/24
See application file for complete search history.

(56) References Cited

U.S. PATENT DOCUMENTS 3,143,742 A   8/1964   Cromie
3,334,629 A   8/1967   Cohn
(Continued)

FOREIGN PATENT DOCUMENTS

CN   101011298 A   8/2007
DE   3640745 A1    6/1987
(Continued)

OTHER PUBLICATIONS

European Search Report issued in EP Application No. 11425310, completed May 31, 2012, 8 pages.
(Continued)

*Primary Examiner* — Jason-Dennis Stewart
(74) *Attorney, Agent, or Firm* — Faegre Baker Daniels LLP

(57) ABSTRACT

A method of repairing a native cardiac valve such as the aortic valve includes positioning a cardiac valve prosthesis at an implantation site proximate the native cardiac valve to be repaired. The cardiac valve prosthesis includes an armature and a plurality of prosthetic valve leaflets, the armature including first and second annular elements, a plurality of anchor members extending between the first and second annular elements, and a plurality of valve support members extending from at least one of the first and second annular elements, the plurality of prosthetic valve leaflets being coupled to and supported by the valve support members. The method further includes radially expanding the cardiac valve prosthesis such that each of the anchor members arches radially outward from the first annular element to the second annular element and engages a wall of a respective one of a plurality of native Valsalva sinuses located distal to the native cardiac valve so as to enable anchorage of the cardiac valve prosthesis at the implantation site.

10 Claims, 6 Drawing Sheets

Related U.S. Application Data continuation of application No. 12/139,686, filed on Jun. 16, 2008, now Pat. No. 8,539,662, which is a continuation of application No. 11/352,021, filed on Feb. 10, 2006, now Pat. No. 7,857,845.

(52) U.S. Cl.
CPC ....... *A61F 2/848* (2013.01); *A61F 2210/0014* (2013.01); *A61F 2220/0008* (2013.01); *A61F 2220/0075* (2013.01); *A61F 2230/0054* (2013.01); *A61F 2250/001* (2013.01); *Y10T 29/49833* (2015.01)

(56) References Cited

U.S. PATENT DOCUMENTS

| | | |
|---|---|---|
| 3,363,442 A | 1/1968 | Kennedy et al. |
| 3,409,013 A | 11/1968 | Berry |
| 3,540,431 A | 11/1970 | Kazi |
| 3,546,710 A | 12/1970 | Ivanovich et al. |
| 3,574,865 A | 4/1971 | Hamaker |
| 3,587,115 A | 6/1971 | Shiley |
| 3,608,097 A | 9/1971 | Bellhouse et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,744,060 A | 7/1973 | Bellhouse et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,086,665 A | 5/1978 | Poirier |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,477,930 A | 10/1984 | Totten et al. |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,624,822 A | 11/1986 | Arru et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,692,164 A | 9/1987 | Dzemeshkevich et al. |
| 4,710,192 A | 12/1987 | Liotta et al. |
| 4,733,665 A | 3/1988 | Palmaz |
| 4,758,151 A | 7/1988 | Arru et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,042,161 A | 8/1991 | Hodge |
| 5,047,041 A | 9/1991 | Samuels |
| 5,059,177 A | 10/1991 | Towne et al. |
| 5,061,273 A | 10/1991 | Yock |
| 5,084,151 A | 1/1992 | Vallana et al. |
| 5,085,635 A | 2/1992 | Cragg |
| 5,089,015 A | 2/1992 | Ross |
| 5,123,919 A | 6/1992 | Sauter et al. |
| 5,133,845 A | 7/1992 | Vallana et al. |
| 5,139,515 A | 8/1992 | Robicsek |
| 5,152,771 A | 10/1992 | Sabbaghian et al. |
| 5,161,547 A | 11/1992 | Tower |
| 5,163,953 A | 11/1992 | Vince |
| 5,163,954 A | 11/1992 | Curcio et al. |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,300,086 A | 4/1994 | Gory et al. |
| 5,314,468 A | 5/1994 | Ramos Martinez |
| 5,327,774 A | 7/1994 | Nguyen et al. |
| 5,332,402 A | 7/1994 | Teitelbaum |
| 5,350,398 A | 9/1994 | Pavcnik et al. |
| 5,360,014 A | 11/1994 | Sauter et al. |
| 5,370,684 A | 12/1994 | Vallana et al. |
| 5,370,685 A | 12/1994 | Stevens |
| 5,387,247 A | 2/1995 | Vallana et al. |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,423,886 A | 6/1995 | Arru et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,296 A | 2/1996 | Love et al. |
| 5,489,297 A | 2/1996 | Duran |
| 5,496,346 A | 3/1996 | Horzewski et al. |
| 5,507,767 A | 4/1996 | Maeda et al. |
| 5,522,884 A | 6/1996 | Wright |
| 5,545,209 A | 8/1996 | Roberts et al. |
| 5,545,211 A | 8/1996 | An et al. |
| 5,545,214 A | 8/1996 | Stevens |
| 5,545,215 A | 8/1996 | Duran |
| 5,554,185 A | 9/1996 | Block et al. |
| 5,560,487 A | 10/1996 | Starr |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,669,919 A | 9/1997 | Sanders et al. |
| 5,672,169 A | 9/1997 | Verbeek |
| 5,674,277 A | 10/1997 | Freitag |
| 5,693,066 A | 12/1997 | Rupp et al. |
| 5,695,498 A | 12/1997 | Tower |
| 5,698,307 A | 12/1997 | Levy |

(56) References Cited

U.S. PATENT DOCUMENTS

| | | |
|---|---|---|
| 5,702,368 A | 12/1997 | Stevens et al. |
| 5,712,953 A | 1/1998 | Langs |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,776,187 A | 7/1998 | Krueger et al. |
| 5,782,809 A | 7/1998 | Umeno et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,405 A | 9/1998 | Vanney et al. |
| 5,810,873 A | 9/1998 | Morales |
| 5,814,096 A | 9/1998 | Lam et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,843,244 A | 12/1998 | Pelton et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Twoer |
| 5,860,996 A | 1/1999 | Urban et al. |
| 5,861,028 A | 1/1999 | Angell |
| 5,868,783 A | 2/1999 | Tower |
| 5,876,436 A | 3/1999 | Vanney et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,891,195 A | 4/1999 | Klostermeyer et al. |
| 5,906,619 A | 5/1999 | Olson et al. |
| 5,907,893 A | 6/1999 | Zadno Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,947,993 A | 9/1999 | Morales |
| 5,951,540 A | 9/1999 | Verbeek |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,972,016 A | 10/1999 | Morales |
| 5,980,570 A | 11/1999 | Simpson |
| 5,984,957 A | 11/1999 | Laptewicz, Jr. et al. |
| 5,997,573 A | 12/1999 | Quijano et al. |
| 6,010,531 A | 1/2000 | Donlon et al. |
| 6,019,739 A | 2/2000 | Rhee et al. |
| 6,019,790 A | 2/2000 | Holmberg et al. |
| 6,022,370 A | 2/2000 | Tower |
| 6,024,737 A | 2/2000 | Morales |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV et al. |
| 6,051,002 A | 4/2000 | Morales |
| 6,051,014 A | 4/2000 | Jang |
| 6,051,104 A | 4/2000 | Oriaran et al. |
| 6,059,809 A | 5/2000 | Amor et al. |
| 6,059,827 A | 5/2000 | Fenton, Jr. |
| 6,063,102 A | 5/2000 | Morales |
| 6,110,200 A | 8/2000 | Hinnenkamp |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,187,016 B1 | 2/2001 | Hedges et al. |
| 6,197,143 B1 | 3/2001 | Bodnar |
| 6,200,336 B1 | 3/2001 | Pavcnik et al. |
| 6,202,272 B1 | 3/2001 | Jackson |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,110 B1 | 8/2001 | Morales |
| 6,277,555 B1 | 8/2001 | Duran et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,302,906 B1 | 10/2001 | Goicoechea et al. |
| 6,309,382 B1 | 10/2001 | Garrison et al. |
| 6,309,383 B1 | 10/2001 | Campbell et al. |
| 6,309,417 B1 | 10/2001 | Spence et al. |
| 6,312,462 B1 | 11/2001 | McDermott et al. |
| 6,338,735 B1 | 1/2002 | Stevens |
| 6,348,063 B1 | 2/2002 | Yassour et al. |
| 6,350,277 B1 | 2/2002 | Kocur |
| 6,350,281 B1 | 2/2002 | Rhee |
| 6,352,547 B1 | 3/2002 | Brown et al. |
| 6,352,554 B2 | 3/2002 | De Paulis |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,387,117 B1 | 5/2002 | Arnold, Jr. et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,481,262 B2 | 11/2002 | Ching et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,506,201 B2 | 1/2003 | Di Caprio et al. |
| 6,508,833 B2 | 1/2003 | Pavcnik et al. |
| 6,510,722 B1 | 1/2003 | Ching et al. |
| 6,527,800 B1 | 3/2003 | McGuckin, Jr. et al. |
| 6,530,949 B2 | 3/2003 | Konya et al. |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,598,307 B2 | 7/2003 | Love et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,629,350 B2 | 10/2003 | Motsenbocker |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |

(56) References Cited

U.S. PATENT DOCUMENTS

| | | |
|---|---|---|
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,692 B2 | 1/2004 | Rabkin et al. |
| 6,676,698 B2 | 1/2004 | McGuckin, Jr. et al. |
| 6,678,962 B1 | 1/2004 | Love et al. |
| 6,679,893 B1 | 1/2004 | Tran |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,716,241 B2 | 4/2004 | Wilder et al. |
| 6,719,789 B2 | 4/2004 | Cox |
| 6,726,713 B2 | 4/2004 | Schaldach, Jr. et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,161 B2 | 8/2004 | Brown et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,324 B2 | 1/2005 | Stobie |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,915,560 B2 | 7/2005 | Austin |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,966,924 B2 | 11/2005 | Holmberg |
| 6,968,607 B2 | 11/2005 | Motsenbocker |
| 6,974,474 B2 | 12/2005 | Pavcnik et al. |
| 6,974,476 B2 | 12/2005 | McGuckin, Jr. et al. |
| 6,981,982 B2 | 1/2006 | Armstrong et al. |
| 6,986,742 B2 | 1/2006 | Hart et al. |
| 6,988,881 B2 | 1/2006 | Motsenbocker et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,007,396 B2 | 3/2006 | Rudko et al. |
| 7,018,401 B1 | 3/2006 | Hyodoh et al. |
| 7,018,404 B2 | 3/2006 | Holmberg et al. |
| 7,018,406 B2 | 3/2006 | Seguin et al. |
| 7,021,114 B2 | 4/2006 | Perreault |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,069,794 B2 | 7/2006 | Motsenbocker et al. |
| 7,097,659 B2 | 8/2006 | Woolfson et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheimer |
| 7,252,682 B2 | 8/2007 | Seguin |
| 7,255,706 B2 | 8/2007 | Rosengart |
| 7,258,698 B2 | 8/2007 | Lemmon |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,484 B2 | 3/2008 | Schoon et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,357,814 B2 | 4/2008 | Gabbay |
| 7,367,984 B2 | 5/2008 | Kulcinski et al. |
| 7,374,571 B2 | 5/2008 | Pease et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,384,411 B1 | 6/2008 | Condado |
| 7,393,360 B2 | 7/2008 | Spenser et al. |
| 7,427,291 B2 | 9/2008 | Liddicoat et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 | 11/2009 | Case et al. |
| 7,682,390 B2 | 3/2010 | Seguin |
| 7,708,775 B2 | 5/2010 | Rowe et al. |
| 7,780,726 B2 | 8/2010 | Seguin |
| 7,785,341 B2 | 8/2010 | Forster et al. |
| 7,806,919 B2 | 10/2010 | Bloom et al. |
| 7,857,845 B2 | 12/2010 | Stacchino et al. |
| 7,972,378 B2 | 7/2011 | Tabor et al. |
| 7,981,153 B2 | 7/2011 | Fogarty et al. |
| 8,043,360 B2 | 10/2011 | McNamara et al. |
| 8,083,793 B2 | 12/2011 | Lane et al. |
| 8,109,996 B2 | 2/2012 | Stacchino et al. |
| 8,211,169 B2 | 7/2012 | Lane et al. |
| 8,535,373 B2 | 9/2013 | Stacchino et al. |
| 8,539,662 B2 | 9/2013 | Stacchino et al. |
| 8,540,768 B2 | 9/2013 | Stacchino et al. |
| 8,834,563 B2 | 9/2014 | Righini |
| 9,161,836 B2 | 10/2015 | Rolando et al. |
| 9,248,017 B2 | 2/2016 | Rolando et al. |
| 9,289,289 B2 | 3/2016 | Rolando et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |

(56) References Cited

U.S. PATENT DOCUMENTS

| | | |
|---|---|---|
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2001/0049558 A1 | 12/2001 | Liddicoat et al. |
| 2002/0010508 A1 | 1/2002 | Chobotov |
| 2002/0029014 A1 | 3/2002 | Jayaraman |
| 2002/0029783 A1 | 3/2002 | Stevens et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0128702 A1 | 9/2002 | Menz et al. |
| 2002/0129820 A1 | 9/2002 | Ryan et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161377 A1 | 10/2002 | Rabkin |
| 2002/0161392 A1 | 10/2002 | Dubrul |
| 2002/0161394 A1 | 10/2002 | Macoviak et al. |
| 2002/0183839 A1 | 12/2002 | Garrison et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0114913 A1 | 6/2003 | Spenser et al. |
| 2003/0125795 A1 | 7/2003 | Pavcnik et al. |
| 2003/0125805 A1 | 7/2003 | Johnson et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191528 A1 | 10/2003 | Quijano et al. |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0073301 A1 | 4/2004 | Donlon et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0123437 A1 | 7/2004 | Kokish |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0193259 A1 | 9/2004 | Gabbay |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |

(56) References Cited

U.S. PATENT DOCUMENTS

| | | |
|---|---|---|
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0166389 A1 | 8/2005 | Perreault et al. |
| 2005/0187616 A1 | 8/2005 | Realyvasquez |
| 2005/0197695 A1 | 9/2005 | Stacchino et al. |
| 2005/0197696 A1 | 9/2005 | Gomez Duran |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0229670 A1 | 10/2005 | Perreault |
| 2005/0234537 A1 | 10/2005 | Edin |
| 2005/0234546 A1 | 10/2005 | Nugent et al. |
| 2005/0240200 A1 | 10/2005 | Bergheim |
| 2005/0240256 A1 | 10/2005 | Austin |
| 2005/0240263 A1 | 10/2005 | Fogarty et al. |
| 2005/0261759 A1 | 11/2005 | Lambrecht et al. |
| 2005/0267529 A1 | 12/2005 | Crockett et al. |
| 2005/0283232 A1 | 12/2005 | Gabbay |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074486 A1 | 4/2006 | Liddicoat et al. |
| 2006/0085060 A1 | 4/2006 | Campbell |
| 2006/0089711 A1 | 4/2006 | Dolan |
| 2006/0095117 A1 | 5/2006 | Popelar et al. |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0190017 A1 | 8/2006 | Cyr et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0253134 A1 | 11/2006 | Ortiz et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0265855 A1 | 11/2006 | Stenzel |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0027534 A1 | 2/2007 | Bergheim et al. |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0056346 A1 | 3/2007 | Spenser et al. |
| 2007/0061009 A1 | 3/2007 | Spenser et al. |
| 2007/0073387 A1 | 3/2007 | Forster et al. |
| 2007/0073392 A1 | 3/2007 | Heyninck-Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100356 A1 | 5/2007 | Lucatero et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112415 A1 | 5/2007 | Bartlett |
| 2007/0112422 A1 | 5/2007 | Dehdashtian |
| 2007/0118209 A1 | 5/2007 | Strecker |
| 2007/0118215 A1 | 5/2007 | Moaddeb |
| 2007/0142968 A1 | 6/2007 | Prisco et al. |
| 2007/0162102 A1 | 7/2007 | Ryan et al. |
| 2007/0162113 A1 | 7/2007 | Sharkawy et al. |
| 2007/0168024 A1 | 7/2007 | Khairkhahan |
| 2007/0173861 A1 | 7/2007 | Strommer et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |

(56) References Cited

U.S. PATENT DOCUMENTS

| | | |
|---|---|---|
| 2007/0265701 A1 | 11/2007 | Gurskis et al. |
| 2007/0270944 A1 | 11/2007 | Bergheim et al. |
| 2007/0288000 A1 | 12/2007 | Bonan |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262593 A1 | 10/2008 | Ryan et al. |
| 2008/0262603 A1 | 10/2008 | Giaquinta et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192603 A1 | 7/2009 | Ryan |
| 2009/0198316 A1 | 8/2009 | Laske et al. |
| 2009/0209955 A1 | 8/2009 | Forster et al. |
| 2009/0210025 A1 | 8/2009 | Ameri |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0254165 A1 | 10/2009 | Tabor et al. |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0249661 A1 | 9/2010 | Righini et al. |
| 2010/0256723 A1 | 10/2010 | Murray |
| 2010/0262043 A1 | 10/2010 | Sauter et al. |
| 2010/0274351 A1 | 10/2010 | Rolando et al. |
| 2010/0292782 A1 | 11/2010 | Giannetti et al. |
| 2011/0082539 A1 | 4/2011 | Suri |
| 2011/0288636 A1 | 11/2011 | Rolando et al. |
| 2012/0172982 A1 | 7/2012 | Stacchino et al. |
| 2013/0172991 A1 | 7/2013 | Rolando et al. |
| 2013/0325112 A1 | 12/2013 | Stacchino et al. |
| 2013/0345800 A1 | 12/2013 | Stacchino et al. |
| 2014/0052243 A1 | 2/2014 | Rolando et al. |
| 2014/0052244 A1 | 2/2014 | Rolando et al. |
| 2014/0350666 A1 | 11/2014 | Righini |
| 2015/0148895 A1 | 5/2015 | Stacchino et al. |

FOREIGN PATENT DOCUMENTS

| | | |
|---|---|---|
| DE | 19532846 A1 | 3/1997 |
| DE | 19546692 C2 | 6/1997 |
| DE | 29911694 U1 | 9/1999 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 10301026 A1 | 2/2004 |
| DE | 19857887 A1 | 5/2005 |
| DE | 102004019254 B3 | 11/2005 |
| EP | 0133420 B1 | 2/1988 |
| EP | 0155245 B1 | 5/1990 |
| EP | 0515324 B1 | 11/1992 |
| EP | 0401199 B1 | 1/1995 |
| EP | 0502410 B1 | 10/1995 |
| EP | 0850607 A1 | 7/1998 |
| EP | 1057460 A1 | 12/2000 |
| EP | 0778009 B1 | 7/2002 |
| EP | 1330213 B1 | 7/2003 |
| EP | 1259194 B1 | 2/2005 |
| EP | 1214020 B1 | 3/2005 |
| EP | 1353420 B1 | 3/2005 |
| EP | 1088529 B1 | 6/2005 |
| EP | 1014896 B1 | 11/2005 |
| EP | 1469797 A1 | 11/2005 |
| EP | 1603493 A2 | 12/2005 |
| EP | 1174098 B1 | 3/2006 |
| EP | 1600127 B1 | 11/2006 |
| EP | 1255510 A1 | 4/2007 |
| EP | 1143882 B1 | 12/2007 |

(56) References Cited

FOREIGN PATENT DOCUMENTS

| | | |
|---|---|---|
| EP | 1913901 A1 | 4/2008 |
| EP | 1690515 B1 | 7/2008 |
| EP | 1570809 B1 | 1/2009 |
| EP | 2047824 A1 | 4/2009 |
| EP | 2055266 A2 | 5/2009 |
| EP | 1370201 B1 | 9/2009 |
| EP | 2119417 A2 | 11/2009 |
| EP | 2133039 A2 | 12/2009 |
| EP | 2246011 A1 | 3/2010 |
| FR | 2788217 A1 | 7/2000 |
| FR | 2815844 A1 | 1/2003 |
| GB | 2083362 A | 3/1982 |
| GB | 2056023 A | 8/1983 |
| GB | 2433700 A | 12/2007 |
| JP | 11332997 A | 12/1999 |
| NL | 1017275 C2 | 8/2002 |
| SU | 127508 A1 | 11/1986 |
| WO | WO9209247 A1 | 6/1992 |
| WO | WO9529640 A1 | 11/1995 |
| WO | WO9639942 A1 | 12/1996 |
| WO | WO9724989 A1 | 7/1997 |
| WO | WO9814138 A1 | 4/1998 |
| WO | WO9817202 A1 | 4/1998 |
| WO | WO9829057 A1 | 7/1998 |
| WO | WO9913802 A1 | 3/1999 |
| WO | W09953864 A1 | 10/1999 |
| WO | WO9953866 A1 | 10/1999 |
| WO | WO9955255 A1 | 11/1999 |
| WO | WO9956665 A1 | 11/1999 |
| WO | WO0006052 A1 | 2/2000 |
| WO | WO0021464 A1 | 4/2000 |
| WO | WO0030565 A1 | 6/2000 |
| WO | WO0041652 A1 | 7/2000 |
| WO | WO0044313 A1 | 8/2000 |
| WO | WO0047136 A1 | 8/2000 |
| WO | WO0047139 A1 | 8/2000 |
| WO | WO0062714 A1 | 10/2000 |
| WO | WO0062716 A1 | 10/2000 |
| WO | WO0121076 A1 | 3/2001 |
| WO | WO0121107 A1 | 3/2001 |
| WO | WO0121110 A1 | 3/2001 |
| WO | WO0135870 A1 | 5/2001 |
| WO | WO0149213 A2 | 7/2001 |
| WO | WO0154625 A1 | 8/2001 |
| WO | WO0162189 A1 | 8/2001 |
| WO | WO0164137 A1 | 9/2001 |
| WO | WO0176510 A2 | 10/2001 |
| WO | WO0211646 A1 | 2/2002 |
| WO | WO0222054 A1 | 3/2002 |
| WO | WO0236048 A1 | 5/2002 |
| WO | WO02041789 A2 | 8/2002 |
| WO | WO0121103 A2 | 10/2002 |
| WO | WO02076348 A1 | 10/2002 |
| WO | WO02092257 A1 | 11/2002 |
| WO | WO02047575 A2 | 12/2002 |
| WO | WO03011195 A2 | 2/2003 |
| WO | WO03047468 A1 | 6/2003 |
| WO | WO03003943 A2 | 11/2003 |
| WO | WO03094797 A1 | 11/2003 |
| WO | WO03003949 A2 | 1/2004 |
| WO | WO2004019825 A1 | 3/2004 |
| WO | WO2004082527 A2 | 9/2004 |
| WO | WO2004089250 A1 | 10/2004 |
| WO | WO2005004753 A1 | 1/2005 |
| WO | WO2004091455 A2 | 2/2005 |
| WO | WO2005046528 A1 | 5/2005 |
| WO | WO2005062980 A2 | 7/2005 |
| WO | WO2005082578 A1 | 9/2005 |
| WO | WO2006005015 A2 | 1/2006 |
| WO | WO2006026371 A1 | 3/2006 |
| WO | WO2006044679 A1 | 4/2006 |
| WO | WO2006086135 A2 | 8/2006 |
| WO | WO2006088712 A1 | 8/2006 |
| WO | WO2006093795 A1 | 9/2006 |
| WO | WO2006117016 A1 | 11/2006 |
| WO | WO2006124649 A2 | 11/2006 |
| WO | WO2006127089 A1 | 11/2006 |
| WO | WO2006127765 A1 | 11/2006 |
| WO | WO2006135831 A1 | 12/2006 |
| WO | WO2006136930 A1 | 12/2006 |
| WO | WO2007009117 A1 | 1/2007 |
| WO | WO2007053243 A2 | 5/2007 |
| WO | WO2007030825 A2 | 6/2007 |
| WO | WO2007071436 A2 | 6/2007 |
| WO | WO2007130537 A1 | 11/2007 |
| WO | WO2006007401 A2 | 1/2008 |
| WO | WO0121097 A2 | 3/2008 |
| WO | WO2008028569 A1 | 3/2008 |
| WO | WO2008035337 A2 | 3/2008 |
| WO | WO2008047354 A2 | 4/2008 |
| WO | W02008070797 A2 | 6/2008 |
| WO | WO2008089365 A2 | 7/2008 |
| WO | WO2008138584 A1 | 11/2008 |
| WO | WO2008150529 A1 | 12/2008 |
| WO | WO2009002548 A1 | 12/2008 |
| WO | WO2009024716 A2 | 2/2009 |
| WO | WO2009029199 A1 | 3/2009 |
| WO | WO2009042196 A2 | 4/2009 |
| WO | WO2009045331 A1 | 4/2009 |
| WO | WO2009045338 A1 | 4/2009 |
| WO | WO2009081389 A2 | 5/2009 |
| WO | WO2009091509 A1 | 7/2009 |
| WO | WO2009094188 A2 | 7/2009 |
| WO | WO2009111241 A2 | 9/2009 |

OTHER PUBLICATIONS

EP Communication issued in EP 07112385 on Jul. 30, 2009.
Extended European Search Report issued in EP 07106697, mailed Aug. 21, 2007, 6 pages.
Extended European Search Report issued in EP 07112385, mailed Apr. 1, 2008, 11 pages.
Extended European Search Report issued in EP 10168449, dated Aug. 19, 2010, 3 pages.
International Search Report and Written Opinion issued in PCT/US2010/028873, dated Jun. 15, 2010, 11 pages.
Partial European Search Report issued in EP 07112385, mailed Jan. 4, 2008, 5 pages.
Andersen, H.R. et al, "Transluminal implantation of artificial heart valves. Description of a new expandable aortic valve and initial results with implantation by catheter technique in closed chest pigs," Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. I 664-I 669.
Bonhoefer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

(56) References Cited

OTHER PUBLICATIONS

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Inserion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease,"Cardiovascular Pathology 15 (2006) 123-129.
Decision Rejecting Opposition dated Oct. 19, 2011, filed in EP Patent 1690515, 22 pages.
Definition of Hinge downloaded from Voculabulary.com, received at the EPO on Dec. 18, 2012, 1 page.
Definition of Hinge, downloaded from www.meriam-webster.com on Jan. 31, 2013, 3 pages.
Definition of Minimum, downloaded from www.meriam-webster.com on Jan. 31, 2013, 2 pages.
European Search Report issued in EP 10183557, mailed Apr. 11, 2011, 7 pages.
European Search Report issued in EP App No. 08165227, dated Mar. 13, 2009.
European Search Report issued in EP Application No. 05004289, dated Jun. 2, 2005, 3 pages.
European Search Report issued in EP Application No. 06101425, dated May 3, 2006, 6 pages.
European Search Report issued in EP Application No. 08150075, dated Mar. 27, 2008, 6 pages.
European Search Report issued in EP Application No. 1142502.9, dated Aug. 17, 2011, 5 pages.
European Search Report issued in EP Application No. 11425030, dated Aug. 10, 2011, 5 pages.
European Search Report issued in EP Publication No. 1570809 (EP App No. 05004289.4) dated Jan. 5, 2007, 5 pages.
Extended European Search Report issued in EP 09179414, dated Oct. 18, 2010, 8 pages.
Extended European Search Report issued in EP Application 09158822, dated Sep. 29, 2009, 5 pages.
Grube, Eberhard et al., Case Report entitled "First Report on a Human Percutaneous Transluminal Implantation of a Self-Expanding Valve Prosthesis for Interventional Treatment of Aortic Valve Stenosis", Valvular Heart Disease, Catheterization and Cardiovascular Interventions, 2005, 66:465-469.
Hanzel et al., "Complications of percutaneous aortic valve replacement experience with the CriberEdwards Tm percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
International Search Report and Written Opinion issued in PCT/IB2012/050604, mailed Jul. 26, 2012, 16 pages.
International Search Report and Written Opinion issued in PCT/IB2012/050608, mailed Jul. 24, 2012, 9 pages.
International Search Report issued in international Application No. PCT/I B2006/000967, published as WO2006/085225, mailed Jul. 6, 2006.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Perutaneous Implantation of Pulmonary Valves," Expert Review of Cardiovascular Theapy (England), Nov. 2003, pp. 541-548.
Khambadkone, et al, "Percutaneous Pulmonary Valve Implantation: Early and Medium Term Results,"0 Circulation 108 (17 Supplement), Oct. 28, 2003, p. 1V-375.
Khambadkone et al, "Pecutaneous Pulmonary Valve Implantation: Impact of Morphology on Case Selecion," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio-Thoracic Surgery, 28:194-198, 2005.
Medtech Insight, "New Frontiers in Heart Valve Disease," vol. 7, No. 8 (2005).
Minutes of the Oral Proceedings dated Oct. 19, 2011, filed in EP Patent 1690515, 4 pages.
Notice of Appeal dated Dec. 28. 2011 flied in EP Patent 1690515, 3 pages.
Notice of Opposition with Facts, Evidence and Arguments filed in EP Patent 1690515 dated Apr. 30, 2009, 21 pages.
Palacios, "Percutaneous Valve Replacement and Repair, Fiction or Reality?" Journal of American College of Cardiology, vol. 44, No. 8 (2004) pp. 1662-1663.
Pavcnik et al., "Aortic and venous valve for percutaneous insertion," Min. Invas. Ther. & Allied Techol. 2000, vol. 9, pas. 287-292.
Pelton et al., "Medical Uses of Nitinol," Materials Science Forum vols. 327-328, pp. 63-70 (2000).
Response dated Dec. 9, 2009 to the Notice of Opposition filed in EP Patent 1690515 by ATS Medical Inc., 25 pages.
Response dated Mar. 23, 2011 to Summons dated Sep. 16, 2010, filed in EP Patent 1690515, 21 pages.
Response dated Sep. 17, 2012 to Grounds for Appeal dated Feb. 29, 2012, filed in EP Patent 1690515, 48 pages.
Response dated Sep. 17, 2012, Attachment A.
Response dated Sep. 17, 2012, Attachment B.
Roth, Mark, "Old metal heart valve did its job for 42 years", Pittsburgh Post-Gazette, Wednesday Mar. 5, 2008, 3 pages.
Ruiz, "Transcathether Aortic Valve Implantation and Mitral Valve Repair: State of the Art," Pediatric Cardiology, vol. 26, No. 3 (2005).

(56) References Cited

OTHER PUBLICATIONS

Saliba et al, "Treatment of Obstructions of Prosthetic Conduits by Percutaneous Implantation of Stents," Archives des Maldies du Coeur et des Vaisseaux (France), 1999, pp. 591-596.

Stassano et al., "Mid-term results of the valve-on-valve technique for bioprosthetic failure," Eur. J. Cardiothorac. Surg. 2000; 18:453-457.

Statement of Grounds for Appeal dated Feb. 29, 2012, filed in EP Patent 1690515, 41 pages.

Summons dated Apr. 15, 2013 with Facts and Submissions to Date to Attend Oral Proceedings on Nov. 5, 2013, filed in EP Patent 1690515, 13 pages.

Summons dated Sep. 16, 2010 with Facts and Submissions to Date, filed in EP Patent 1690515, 20 pages.

Webb, et al., "Percutaneous Aortic Valve Implantation Retrograde from the Femoral Artery," Circulation (2006), 1 13;842-850.

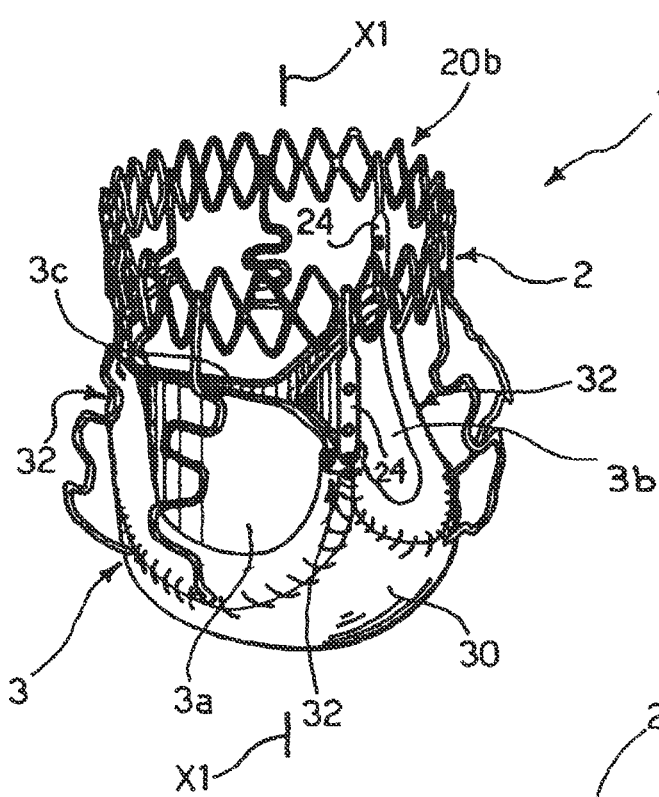
Fig_1
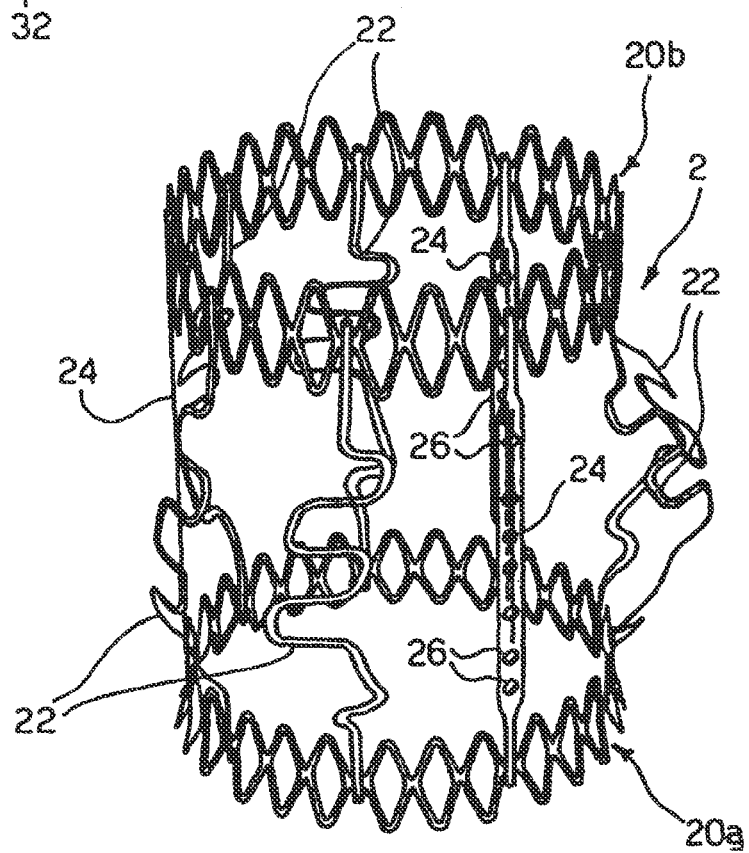
Fig_2

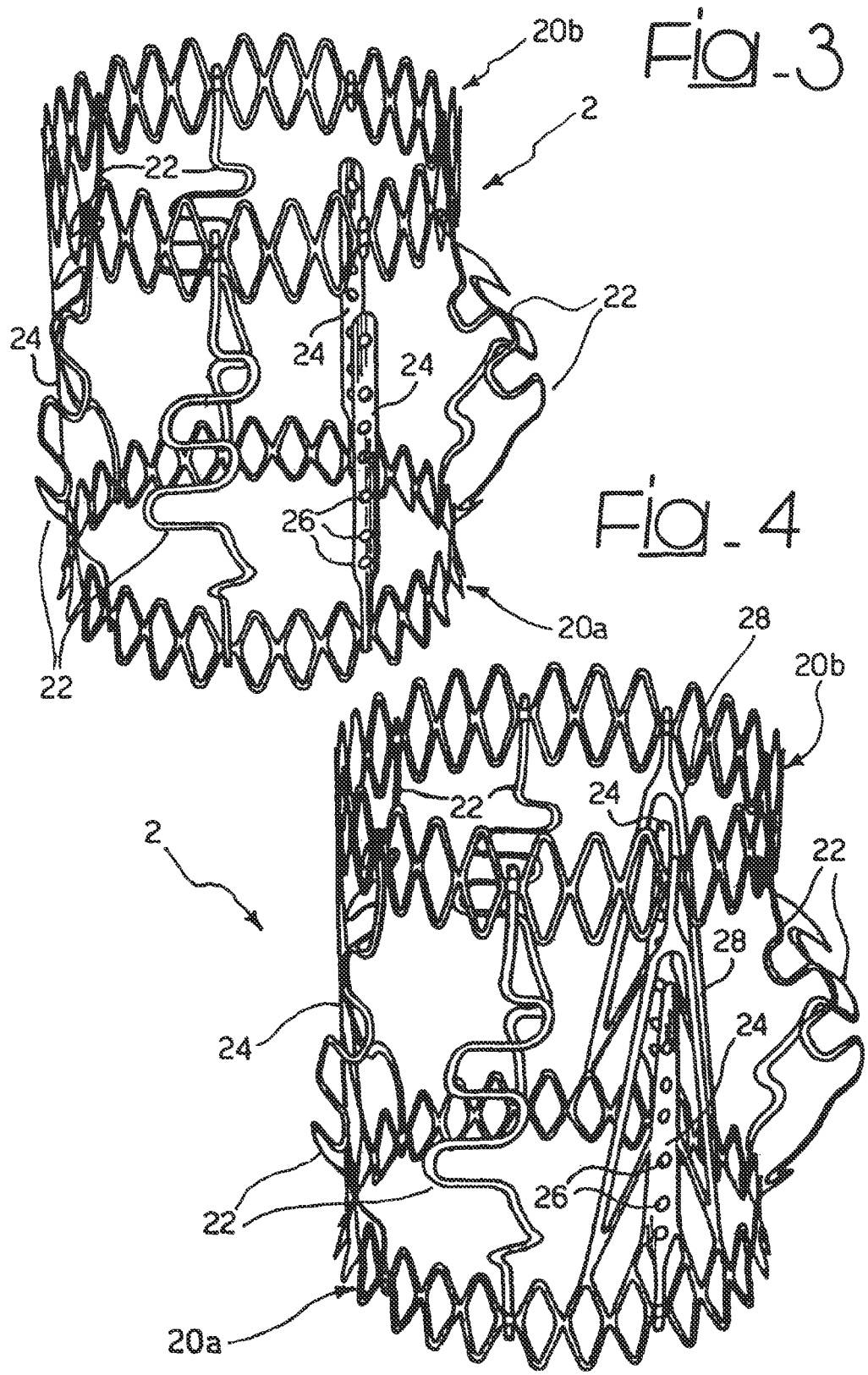

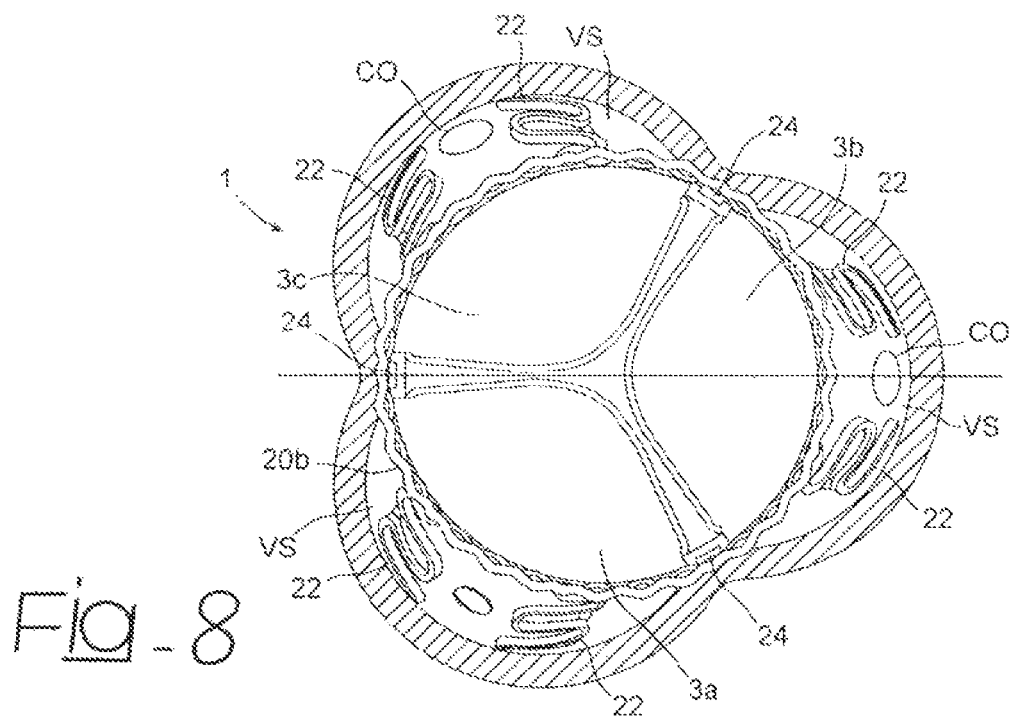
Fig_8
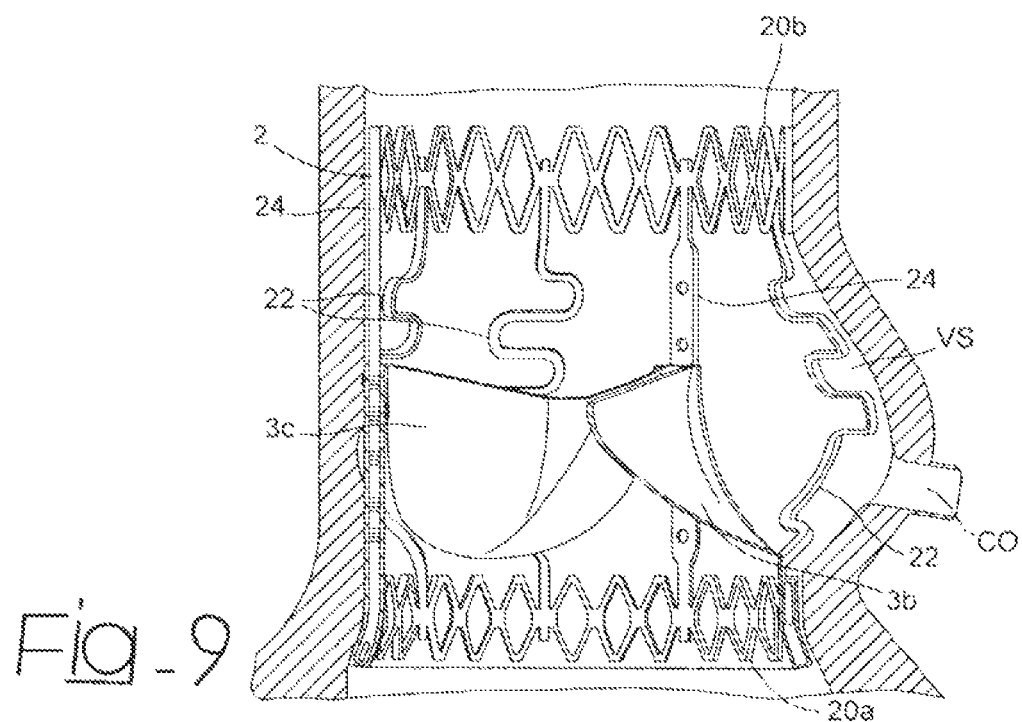
Fig_9

US 9,486,313 B2

CARDIAC VALVE PROSTHESIS

CROSS REFERENCE TO RELATED APPLICATION

This application is a continuation of U.S. patent application Ser. No. 13/972,022, filed on Aug. 21, 2013, which is a continuation of U.S. patent application Ser. No. 13/341,336, filed on Dec. 30, 2011, now U.S. Pat. No. 8,540,768, which is a continuation of application Ser. No. 12/139,686, filed on Jun. 16, 2008, now U.S. Pat. No. 8,539,662, which is a continuation of U.S. patent application Ser. No. 11/352,021 filed on Feb. 10, 2006, now U.S. Pat. No. 7,857,845, which claims priority under 35 U.S.C. §119 from Italian patent application number TO2005/A000074, filed on Feb. 10, 2005. Each of the above-identified applications is hereby incorporated by reference in its entirety for all purposes.

TECHNICAL FIELD

The present invention relates to cardiac-valve prostheses. More specifically, the present invention is directed to a prosthesis that is amenable to a minimally-invasive implantation.

BACKGROUND

Recently, there has been increasing consideration given to the possibility of using, as an alternative to traditional cardiac-valve prostheses, valves designed to be implanted using minimally-invasive surgical techniques or endovascular delivery (the so-called "percutaneous valves"). Implantation of a percutaneous valve (or implantation using thoracic-microsurgery techniques) is a far less invasive act than the surgical operation required for implanting traditional cardiac-valve prostheses. Further details of exemplary percutaneous implantation techniques are provided in U.S. Publication 2002/0042651, U.S. Pat. No. 3,671,979, and U.S. Pat. No. 5,954,766, which are hereby incorporated by reference.

These prosthetic valves typically include an anchoring structure, which is able to support and fix the valve prosthesis in the implantation position, and prosthetic valve elements, generally in the form of leaflets or flaps, which are stably connected to the anchoring structure and are able to regulate blood flow.

Furthermore, the methods of implantation of valves via a percutaneous route or by means of thoracic microsurgery are very frequently irrespective of the effective removal of the natural valve leaflets. Instead, the cardiac valve may be introduced in a position corresponding to the natural annulus and deployed in situ by simply divaricating definitively the natural valve leaflets.

There is a need for a percutaneous valve that does not run the risk of being displaced (dislodged) with respect to the implantation position, as a result of the hydraulic thrust exerted by the blood flow. There is a further need for a percutaneous valve that secures tightly to the flow duct generally defined by the natural valve annulus, such that it resists blood flow around the outside of the percutaneous valve structure.

SUMMARY

In an exemplary embodiment, a cardiac valve prosthesis according to the invention is made so that the entire armature of the valve, or at least the anchorage parts, adhere to the native walls of the implantation site, without interfering with the blood flow, which thus remains practically free. In a preferred way, the anchorage portions moreover have appropriate slits that prevent their interference with the coronary ostia. The anchorage portions and the portions of functional support of the armature can constitute either different parts of a single structure or parts that are structurally distinct from one another. Super-elastic materials can be used in order to obtain a structure that is able to be collapsed for advancement to its implantation site, and to self-recover its expanded geometry once the prosthesis is deployed in the implantation position. The entire armature of the valve, or at least the anchorage parts, can be made even of re-absorbable material, whereas the valve leaflets can be made of biological and/or synthetic tissues, in part colonizable or re-absorbable. In this way, it is possible to obtain anchorage of the device during the period necessary for integration of the valve prosthesis with the physiological tissues of the anatomical site of implantation. Subsequently, there is dissolution of the artificial structure that enables initial anchorage. Amongst the various advantages linked to this solution to be emphasized is the creation of the ideal conditions for a possible prosthetic re-implantation. The armature can include anchorage formations or portions of the supporting structure of the valve flaps made at least partially of shape-memory material (e.g., Nitinol) that enable creation or regulation of the anchorage, i.e., regulation of the modalities and the magnitude of splaying-out of the valve leaflets through control of the memory of the shape-memory material (e.g., by controlling its temperature), according to a mechanism similar to what is described in the document No. EP-A-1 088 529.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

The invention will now be described, purely by way of non-limiting example, with reference to the annexed plate of drawings, in which:

FIG. 1 is a general perspective view of a cardiac-valve prosthesis according to one embodiment of the present invention;

FIGS. 2 to 7 illustrate different embodiments of an armature portion of the cardiac valve prosthesis according to the present invention;

FIGS. 8 and 9 illustrate plan and cross-sectional views, respectively, of the cardiac valve prosthesis implanted at an implantation site in a patient, according to an embodiment of the present invention.

Figure 5:
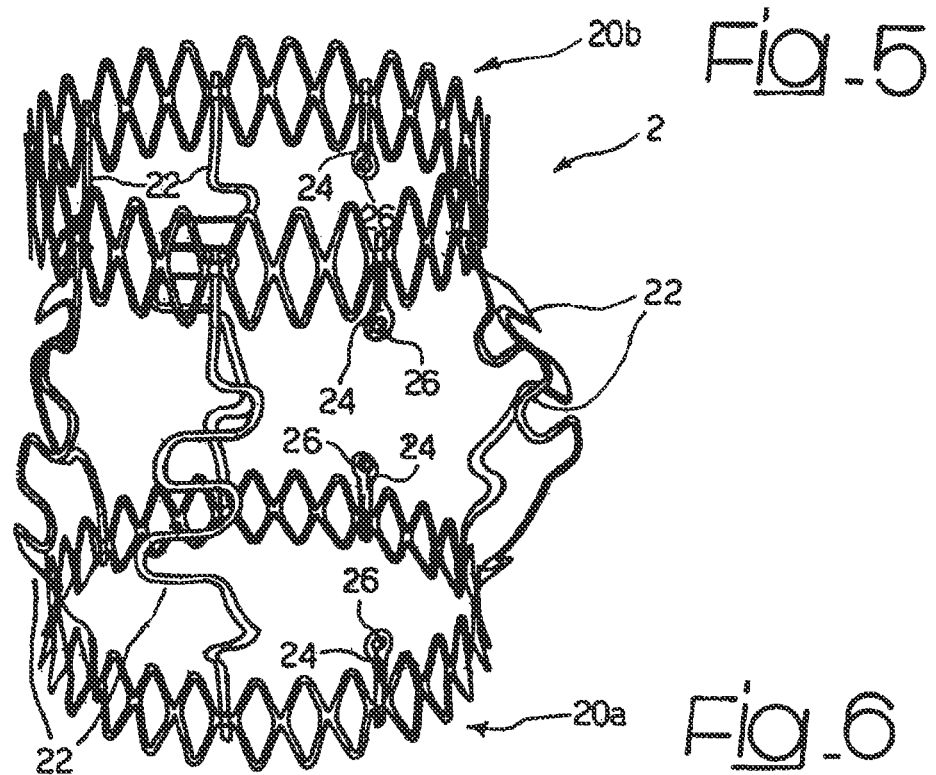

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the figures of the annexed plate of drawings, the reference number 1 designates as a whole a cardiac-valve prosthesis, which can be implanted percutaneously or resorting to techniques of thoracic microsurgery, or else of implantation of a "sutureless" type. Essentially, the prosthesis 1 represented in FIG. 1 includes an armature 2, having the characteristics that emerge more clearly from the representation of FIGS. 2 to 7, and a valve sleeve 3 coupled to the armature 2 and including three valve leaflets 3a, 3b, 3c.

As illustrated in FIG. 2, the armature 2 of the prosthesis 1 can have a general cage-like structure, with a general symmetry of a cylindrical type about a principal axis X1. In percutaneous valves the axis X1 is designed to correspond usually to the principal axis of the distal part of the catheter used for implantation of the prosthesis 1. For the present purpose, the axis X1 can be viewed basically as an entity of a purely geometrical nature. As shown, the armature 2 defines a lumen which operates as a flow tube or duct to accommodate the flow of blood there through. As will be readily apparent to those skilled in the art, a major characteristic of the present invention is the absence of structural elements that can extend in the lumen through which blood flows.

The valve sleeve 3 may be constructed according to various techniques known in the art. For example, techniques for the formation of the valve leaflets, assembly of the valve sleeve and installation thereof on an armature that can be used in the context of the present invention are described in EP-A-0 133 420, EP-A-0 155 245 and EP-A-0 515 324 (all of which are hereby incorporated by reference), the latter document referring to the construction of a cardiac-valve prosthesis of biological tissue of the type commonly referred to as "stentless."

As further illustrated, the valve sleeve 3 includes a base portion 30 with an overall annular pattern, designed to extend from the lower portion of the prosthesis 1, which, in the implantation site, is in a position proximal with respect to the direction of flow of the blood through the prosthesis (from below upwards, as viewed in FIG. 1). Starting from the base portion 30, there extend in an axial direction towards the inside of the structure of the prosthesis 1 three pleat formations 32. The valve leaflets 3a, 3b and 3c extend like a festoon, with a general claw-like conformation, between pairs of pleat formations 32 adjacent to one another.

As illustrated in FIG. 1, each valve leaflet 3a, 3b and 3c has a fluidodynamically proximal edge with an arched pattern, which extends from the base formation 30 and along two adjacent pleat formations 32, and a fluidodynamically distal edge, which extends towards the central orifice of the prosthesis so as to be able to co-operate with the homologous edges of the other valve leaflets. The terms "fluidodynamically proximal" and "fluidodynamically distal" refer to the direction of free flow of the blood through the prosthesis, a direction that is from below upwards, as viewed in the figures of the annexed plate of drawings.

As will be understood by those of ordinary skill in the art, in operation, the valve leaflets 3a, 3b, 3c are able to undergo deformation, divaricating and moving up against the armature 2 so as to enable free flow of the blood through the prosthesis. When the pressure gradient, and hence the direction of flow, of the blood through the prosthesis tends to be reversed, the valve leaflets 3a, 3b, 3c then move into the position represented in FIG. 1, in which they substantially prevent the flow of the blood through the prosthesis. Usually, the valve leaflets 3a, 3b, 3c are made in such a way as to assume spontaneously, in the absence of external stresses, the closed configuration represented in FIG. 1.

FIGS. 2 through 7 depict the armature 2 according to various embodiments of the present invention. Referring first to FIG. 2, it is shown that the armature 2 (which may be made of metal material, such as for example the material commonly referred to as Nitinol) includes two annular elements 20a, 20b, which generally occupy respective end positions within the armature 2. In one embodiment, in the site of implantation of the prosthesis 1, the annular elements 20a and 20b are designed to be located, respectively, upstream and downstream of the sinuses of Valsalva.

During implantation, the prosthesis 1 is advanced towards the implantation site in a radially contracted configuration, with the annular elements 20a and 20b in a radially collapsed configuration. In one embodiment, when so collapsed, the annular elements 20a, 20b have a minimum diameter of about 5 to about 15 mm, according to the technique of implantation for which the prosthesis is designed. Once the prosthesis 1 has reached the implantation site, the annular elements 20a, 20b are made/allowed to expand until they reach their normal expanded configuration, with a diameter that ranges, in one embodiment, from about 18 to about 30 mm.

In order to enable the movement of expansion, the annular elements 20a and 20b are made, according to the illustrated embodiment, with a mesh structure substantially resembling the mesh structure of a stent for angioplasty. It will be appreciated in fact that the annular elements 20a and 20b are designed to perform a movement of radial expansion (with subsequent maintenance of the radially expanded configuration) substantially resembling the movement of expansion in situ of an angioplasty stent.

In the example of embodiment illustrated herein, the annular elements 20a and 20b have a rhomboidal-mesh structure. In other embodiments, the parts 20a, 20b can be made with any structure that is able to ensure the necessary functionality.

In one embodiment, as shown in FIG. 2, the annular element 20a designed to be located in a position proximal with respect to the flow of the blood through the prosthesis 1 (i.e., on the inflow side of the blood in the prosthesis 1 in the conditions of free flow) may have a proximal end that is at least slightly flared outward like an enlarged opening of the flow duct of the blood. This configuration functions to promote a more positive anchorage of the annular element 20a, and in turn, the prosthesis 1, to the valve annulus, thus promoting the perivalvar tightness, improving the haemo-dynamics, and adapting (i.e., radiusing) the lines of blood flow in the ventricular chamber to the flow tube constituted by the valve sleeve.

As shown, the annular elements 20a, 20b are connected to one another by anchor members 22, which in the illustrated embodiment, are generally arched, projecting towards the outside of the prosthesis 1. In one embodiment, the anchor members 22 are designed such that when the prosthesis 1 is positioned at the implantation site, the anchor members 22 can extend on the outside of the sinuses of Valsalva so as to ensure firm anchorage in situ of the prosthesis 1.

With the prosthesis 1 in the radially contracted configuration adopted for implantation, the anchor members 22 are normally maintained in a position (not shown) recalled towards the central axis X1 of the prosthesis 1. This can occur, for example, via a retention means such as a tubular sheath of an implantation catheter through which the radially contracted prosthesis is advanced. Subsequently, once disengaged from the retention means, the anchor members 22 may assume the arched pattern represented in the figures so as to be able to project (protrude), in one embodiment, within the sinuses of Valsalva.

As will be appreciated by those skilled in the art, the sinuses of Valsalva are, in a normal heart, three in number, and are distributed in an approximately angularly uniform way around the root of the artery distal to the semilunar valve (i.e., the aortic or pulmonary valve). Accordingly, as illustrated, the prosthesis 1 may include three anchor members 22 (or three groups of anchor members) set at an angular distance apart of about 120° with respect to the central axis X1 of the prosthesis.

In the exemplary embodiment illustrated, the anchor members 22 are made in the form of ribbon-like elements that extend in a generally sinusoidal or serpentine path, with bends or open loops situated on either side with respect to an ideal line extending approximately in the direction of the generatrices of the overall cylindrical shape of the prosthesis. In another embodiment of the invention, the sinusoidal pattern can be obtained with bends or open loops that extend from one side and from the other with respect to a line that extends in a circumferential direction with respect to the prosthesis. In yet another embodiment, the anchor members 22 may have a mesh structure, for example closed rhomboidal meshes of the same type as the one represented with reference to the annular elements 20a, 20b, or to simple segments of curve lying in roughly radial planes. Additionally, as discussed above, each anchor member 22 can consist either of a single element or of a plurality of elements (e.g., pairs of anchor members 22 as shown in FIGS. 2-7) that extend in a direction in which they are generally set alongside one another.

The annular elements 20a and 20b and the respective anchor members 22 substantially form the basic structure of the armature 2 of the prosthesis 1, which is designed to ensure positioning and anchorage in situ of the prosthesis 1 itself.

Associated then to the annular elements 20a and 20b are further support members, generically designated by 24 in all of FIGS. 2 to 7, which operate to support the valve sleeve 3 on the armature 2 of the prosthesis 1. In the embodiment represented in FIG. 2, the support members 24 are simply represented by three generally flat bars extending between and connecting the annular members 20a, 20b. As further illustrated, the support members 24 are set at an angular distance apart of about 120°, with each generally located at a position that is approximately centrally intermediate the anchor members 22.

As may be appreciated from a comparative examination of FIGS. 1 and 2, the support members 24 are designed to enable the installation of the valve sleeve 3 in a condition such that the base portion 30 thereof is arranged in general in a position around the annular element 20a of the armature 2, while each of the pleat formations or folds 32 in turn embraces one of the elements or support members 24, while the valve leaflets 3a, 3b and 3c extend in a festoon, each between two adjacent support members 24. The general apertured structure both of the annular element 20a and of the support members 24 (note the particular holes designated by 26) enables fixing of the valve sleeve 3 on the armature 2 by, for example, suturing stitches according to known techniques. In the case where flaps of polymeric materials are used, the flaps can be formed directly on the structure, using techniques such as, for example, dip casting.

In this regard, both the armature 2 and the aforesaid suturing stitches can be advantageously provided with a coating of biocompatible carbon material, which may be applied according to the solutions described in U.S. Pat. No. 4,624,822, U.S. Pat. No. 4,758,151, U.S. Pat. No. 5,084,151, U.S. Pat. No. 5,133,845, U.S. Pat. No. 5,370,684, U.S. Pat. No. 5,387,247, and U.S. Pat. No. 5,423,886, the contents of which are hereby incorporated by reference.

The apertured structure of the supporting formations 24, and of the armature 2 in general, means that the armature 2 does not exert any substantial obtrusive effect, preventing, for example, interference in regard to the coronary ostia.

FIG. 3 depicts an alternative embodiment of the armature 2 of the present invention. The variant embodiment represented in FIG. 3 as a whole resembles the embodiment represented in FIG. 2, with the exception that (in the embodiment of FIG. 3) the support members 24 provided for anchorage of the valve sleeve 3 do not extend completely in bridge-like fashion between the two annular parts 20a and 20b. Rather, in the embodiment illustrated in FIG. 3, the support members 24 are projecting elements that extend in cantilever fashion starting from the annular element 20a, and do not reach the annular element 20b. In particular, the lengths of the aforesaid cantilevered support members 24 are determined in such a way as to extend for a length sufficient to enable anchorage of the valve sleeve 3 to the support members 24 at the pleat formations 32. Thus, in one embodiment, the support members 24 do not include any portions other than those portions which operate to support the valve sleeve 3.

FIG. 4 illustrates another embodiment of the armature 2 according to the present invention. As shown, in the embodiment of FIG. 4, like that shown in FIG. 3, the support members 24 project in cantilever fashion from the annular element 20a. As further shown in FIG. 4, in this embodiment, the support members 24 have associated thereto fork-like structures 28. Each fork-like structure 28 has a root portion connected to the annular element 20b and two prongs that extend on either side of the respective support member 24 and then connect up to the annular element 20a on opposite sides with respect to the area in which the support member 24 projects in cantilever fashion from the formation 20a.

As further shown in FIG. 4, in one embodiment, the support members 24 are generally tapered, such that they have widths that decrease gradually moving away from the annular element 20a, that is, in the proximal-to-distal direction with reference to the direction of free flow of the blood through the prosthesis. As will be apparent to those skilled in the art, tapering of the support members 24 may be employed in any of the embodiments illustrated in FIGS. 2 to 4. Similarly, any of the other characteristics of the support members 24 or the anchor members 22, which albeit herein represented are identical to one another in each of the embodiments illustrated, could in actual fact be different from one another. That is, in any embodiment of the valve prosthesis 1, there could coexist, in a single prosthesis, anchor members 22 or support members 24 different from one another, with characteristics drawn from different embodiments amongst the plurality of embodiments illustrated herein.

The solution represented in FIG. 4 generally provides a more rigid anchorage structure as compared to the embodiment of FIG. 3. In the embodiment illustrated in FIG. 4, the fork-like formations 24 effectively fix the axial dimension of the prosthesis 1, which promotes the expansion of the anchor members 22 in the sinuses of Valsalva. At the same time, in the illustrated embodiment of FIG. 4, the support members 24, which operate to facilitate attachment of the valve sleeve 3 to the armature 2, are maintained flexible and of modulatable stiffness.

In the embodiment represented in FIG. 5, the support members 24 are provided in positions corresponding to both of the annular elements 20a, 20b. In this case, however, the support members 24 provided for anchorage of the valve sleeve 3 are reduced to small hooking cantilevers, each provided with an eyelet 26. The eyelets 26 can be used directly for passing and tying the wires that extend from the valve sleeve 30.

Figure 6:
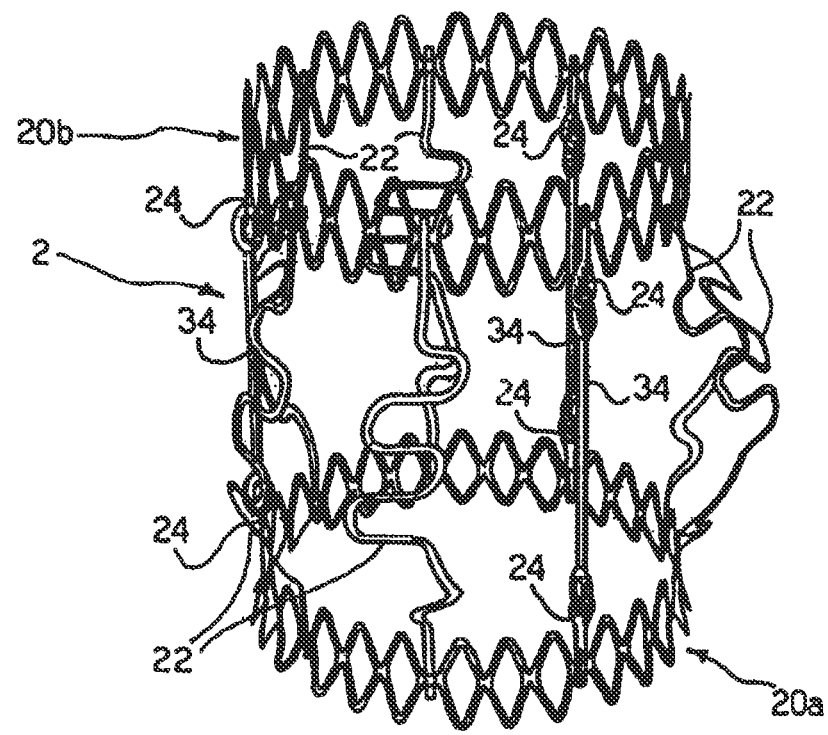

Yet another embodiment is shown in FIG. 6, in which the support members 24 are arranged in opposed pairs, with each of the support members 24 within a pair extending in cantilever fashion from one of the annular elements 20a, 20b and being connected by a connecting element 34. In one embodiment, the connecting elements 34 may have a generally filiform (i.e., relatively long and thin) shape, whereby the connecting elements 34 may be made relatively flexible and thus may provide a flexible connection between the support members 24. In one embodiment, the connecting elements 34 may be made from biocompatible metal alloys (e.g., Nitinol) or polymeric materials suitable for applications in the field of implantations (e.g., acetal resins).

As shown, the overall configuration of the embodiment of FIG. 6 generally resembles, from a geometrical standpoint, the embodiment represented in FIG. 2. The difference lies in the fact that, whereas the support members 24 represented in FIG. 2 are as a whole generally stiff (taking into account the intrinsic flexibility of the material that constitutes them), the connecting elements 34 shown in FIG. 6 may have a filiform shape with a relatively high flexibility. The embodiment illustrated in FIG. 6 thus enables the configuration for hooking of the valve sleeve 3 to the armature 2 of the prosthesis to be rendered elastic/flexible and renders the extent of the anchor members 22 independent of that of the support members 24, thus enabling a greater elasticity of design.

Figure 7:
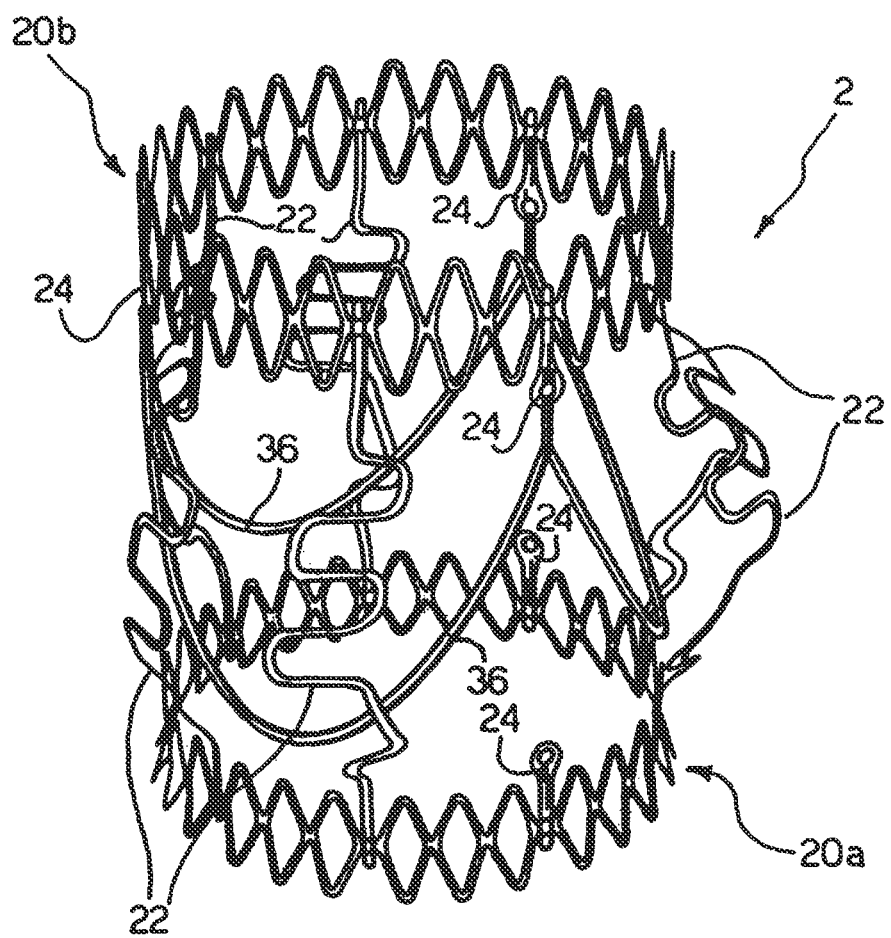

FIG. 7 depicts yet another embodiment of the armature 2, which is otherwise similar to the embodiment illustrated in FIG. 6, except that in the embodiment of FIG. 7, the mutually facing pairs of support members 24 are not connected to each other (as by the connecting members 34 in FIG. 6). Instead, in the embodiment represented in FIG. 7, a supporting element 36 extends between and connects each of the support members 24 extending in cantilever fashion from the annular element 20b. As shown, the supporting elements 36 may extend in a generally festoon-like or catenary path between each of the support members 24 attached to the annular part 20b. The supporting elements 36 are configured such that each can support one of the valve leaflets 3a, 3b, or 3c of the valve sleeve 3. The supporting elements 36 may be made of substantially rigid or flexible materials.

In another embodiment (not shown), the supporting elements 36 may be configured to extend from the support members 24 extending in cantilever fashion from the annular element 20a.

As will be readily understood by those skilled in the art, festoon-like or catenary pattern of the supporting elements 36 may be generally configured to match the homologous pattern of the proximal edges of the valve leaflets 3a, 3b and 3c (see FIG. 1), defining the profile of the edge for anchorage of the functional flaps and, possibly, enabling connection by suture of the aforesaid proximal edges of the valve leaflets to the festoon-like supporting elements 36. This enables the use of relatively simple valve sleeves 3, assigning the formation of the profile of the functional flaps of the valves to the supporting elements 36.

The embodiments of the present invention described herein enables, in the final position of implantation, the entire armature 2 of the prosthesis 1, or at least the anchorage parts, to adhere to the native walls of the implantation site, without interfering with the blood flow, which thus remains practically free. Additionally, the armature 2 and anchor members 22 moreover have a generally apertured structure (for example, appropriate slits), which prevents interference with the coronary ostia.

The anchorage portions and the portions of functional support of the armature 2 can constitute either different parts of a single structure or parts that are structurally distinct from one another. The entire armature 2, or at least the anchorage parts (e.g., the anchor members 22), may be made of re-absorbable material, whereas the valve sleeve 3 can be constituted by biological and/or synthetic tissues, which are in part colonizable or re-absorbable.

Alternatively, as discussed above, the armature 2 can contain anchorage formations (e.g., anchor members 22) made at least partially of shape-memory material (e.g., Nitinol), which enable creation or regulation of the anchorage through the control of the memory of the shape-memory material (e.g., controlling its temperature).

FIGS. 8 and 9 illustrate plan and cross-sectional views, respectively, of the prosthesis 1 in its implanted state in an aortic valve replacement, according to an embodiment of the invention. As shown, and as discussed in detail above, the prosthesis 1 can be implanted such that the annular elements 20a and 20b occupy positions proximal and distal, respectively, of the Valsalva sinuses VS, with the flared proximal end of the annular member 20a forming the proximal entrance of the lumen defined by the armature 2 of the prosthesis 1. In the illustrated embodiment, the anchor members 22 can be arranged in three pairs positioned relative to the sinuses of Valsalva such that the radially projecting portion of each of the anchor members 22 projects into the respective sinus of Valsalva and engages the aortic wall therein. As further shown, the anchor members 22 of each pair can be positioned on opposite sides of the coronary ostia CO in the respective sinuses of Valsalva. Additionally, as discussed above and shown in FIGS. 8 and 9, the serpentine or otherwise generally apertured structure of the anchor members 22 substantially avoids interference with the coronary ostia CO. Finally, as can be seen from FIGS. 8 and 9, the valve leaflets 3a, 3b, 3c can be positioned within the lumen for blood flow formed by the annular elements 20a, 20b, with the support members 24 extending into the lumen by a minimal amount.

The armature 2 of the prosthesis 1, according to one embodiment, is manufactured by first cutting a blank part from a tube of a biocompatible metal (e.g., Nitinol, or a cobaltum-chromium alloy) having an outer diameter which is at an intermediate size between the fully radially contracted and the fully expanded device dimensions. For example, the tube may have an outer diameter of between about 8 mm to about 14 mm. In one embodiment, the tube has a diameter of about 10 mm. In one embodiment, the tube wall may vary between about 0.3 mm to about 0.5 mm, depending on the required stiffness required and the size of the prosthesis 1.

In one embodiment, the final dimension and shape of the framework is achieved by a sequence of expansion cycles. A specific heat treatment is applied after each expansion cycle to homogenize and stress relieve the material, which allows the shape and properties of the structure of the armature 2 to be set. Although the number of forming steps may vary among devices, for the geometries described above with respect to the present invention, and using Nitinol for the tube blank, an exemplary number of forming steps is around three. Among these steps, the first two provide the final diameter of the annular elements 20a, 20b. For example, if the fully-expanded diameter for implantation is 23 mm, the final cylindrical shape of the armature 2 can be achieved using a tube blank of about 10 mm in diameter, a first expansion from about 10 mm to about 18 mm, and a second expansion from about 18 mm to about 23 mm. Optionally, the final diameter can be made slightly larger (e.g. about 25 mm in the previous example) in order to oversize the armature 2 with respect to the physiological annulus, thus imparting a radial force to the wall of the annulus at the nominal implant diameter.

The third forming step is aimed to impart the radially extending shape of the anchor members 22 such that they will fit and anchor within the Valsalva sinuses. The corresponding heat treatment, according to one embodiment, includes exposing the deformed armature 2 to a temperature from about 480° C. to about 550° C., for a time ranging from about 5 minutes to about 30 minutes, depending on the desired final transformation temperature. For example, in order to obtain a super-elastic behavior at 37° C. (the normal working condition in human body) the heat treatments subsequent to the two initial expansion steps may be performed at about 480° C. for a time of about 9 minutes, and the final heat treatment (after the third expansion) is performed at about 500° C. for a time of about 9 minutes.

After the forming process is complete, the armature 2 may undergo one or more surface treatments, for example, sandblasting and electropolishing, to provide a sufficiently smooth surface and to remove the shallow defects. The armature 2 may thereafter be finally exposed to a carbon coating process in order to improve its hemocompatibility.

As shown in FIGS. 8-9, for an aortic valve replacement, the final geometrical shape of the armature 2 will generally approximate the physiological shape and dimension of the aortic root, such that the anchor members 22 generally conform to the walls of the respective Valsalva sinuses VS.

Figure 10:
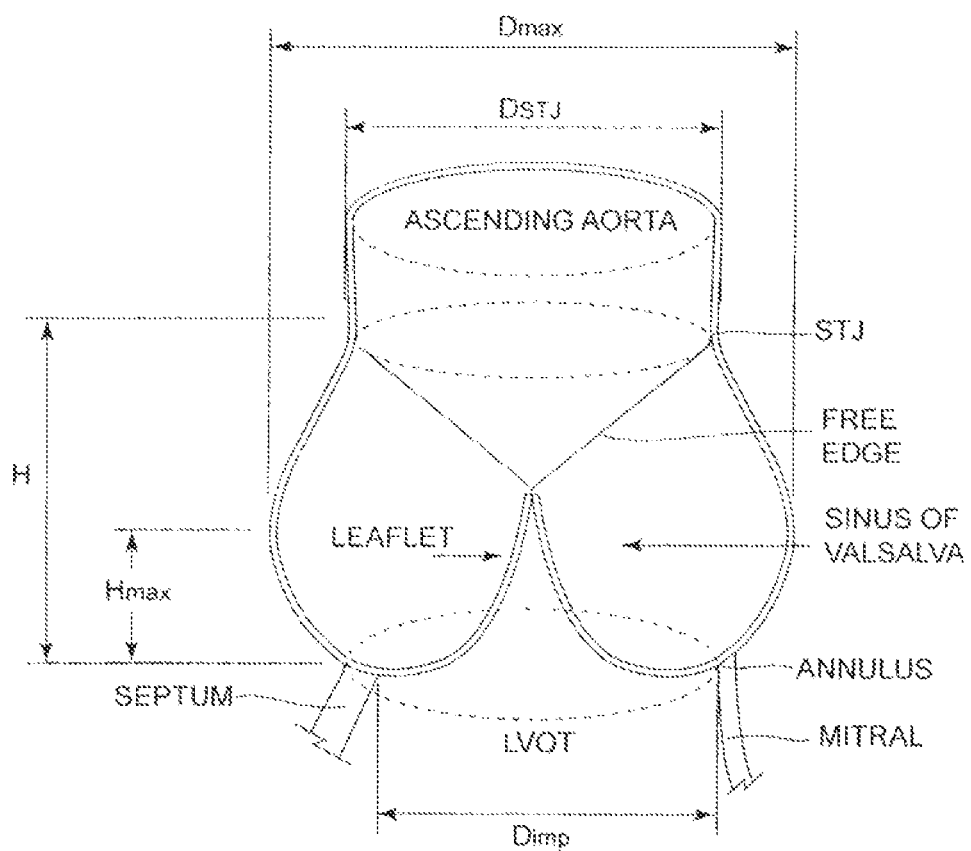
FIG. 10 is a schematic cross-sectional view of an implantation site for the cardiac valve prosthesis according to one embodiment of the present invention.

FIG. 10 shows a schematic cross sectional view of an implantation site for an aortic valve replacement. Referring to FIG. 10, exemplary proportions of the relevant features at the implantation site for an aortic valve replacement are as follows (assuming the annulus diameter Dimp (implanting diameter) equal to 1):

|  | Approximate Minimum | Approximate Maximum |
| --- | --- | --- |
| Height of Valsalva sinuses (H): | 0.8 | 1 |
| Max. diameter of Valsalva sinuses (Dmax): | 1.3 | 1.7 |
| Distance between Valsalva max. diameter and basic annulus plane (Hmax): | 0.3 | 0.5 |
| Diameter at the sino-tubular junction (Dstj): | 0.8 | 1.4 |

According to one exemplary embodiment, H is about 0.9, Dmax is about 1.5, Hmax is about 0.35, and Dstj is about 1.2.

The commissural points of the elastic collapsible valve 3 are mounted to the armature 2 (e.g., by attachment to the support members 24) such that the valve leaflets 3a, 3b, and 3c can fold and expand together. The valve 3, including the valve leaflets 3a, 3b, 3c, can be, for example, a glutaraldehyde fixed pericardium valve which has three cusps that open distally to permit unidirectional blood flow.

In one embodiment, the valve member may use two pericardium sheets. The first sheet forms the three moving cusps, the second sheet coats part of the armature 2 surface so that there is no contact between the armature 2 and the valve leaflets avoiding the risk of abrasion due to repeated impact against the metallic material of the armature 2. In addition, this second sheet redistributes the stress applied by blood pressure on the prosthetic leaflets, avoiding the risk of stress concentration.

The two sheets of pericardium may be stitched together flat using suture thread coated with a film of biocompatible material, and then close in a cylindrical shape. The type of stitch used may be varied to accommodate the directional differences in the forces exerted at each point of the suture, to ensure that the stitches themselves don't become the origin of fatigue fracture lines. The two sheets may be stitched together in a flat position so when the leaflets open they recover their original cylindrical configuration, forming a cylindrical duct.

The elastically collapsible valve sleeve 3 can be mounted on the armature 2 by means of a number of suture stitches. Both of the sheets are useful for attaching the valve sleeve 3 to the armature 2 by stitching.

The valve member can use a tissue fixation and shaping of the leaflets 3a, 3b, 3c by means of a fluidic, atraumatic system with chemicals useful for cross-linking and then may be exposed to a detoxification post treatment to increase long-term performance. An additional pericardium sheet corresponding to base portion 30 of the valve sleeve 3 can be positioned in a generally cylindrical fashion around the annular element 20a so as to improve the sealing capability of the prosthesis 1 to the valve annulus.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:
1. A method of implanting a prosthesis at an implantation site proximate a native aortic valve to be repaired, the implantation site including a valve annulus and three Valsalva sinuses located distal to the valve annulus, the method comprising:
positioning the prosthesis at the implantation site in a radially collapsed configuration, the prosthesis including an armature and a valve connected to the armature, the armature including a proximal portion, a distal portion, and first, second and third Valsalva sinus anchors each extending between and connecting the proximal and distal portions, wherein positioning the prosthesis includes positioning the prosthesis so that the first, second and third Valsalva sinus anchors are each positioned so that they can project into a respective one of the Valsalva sinuses of the implantation site;
radially expanding the prosthesis such that each of the Valsalva sinus anchors arches radially outward from the proximal portion to the distal portion and extends into and engages a wall of a respective one of the Valsalva sinuses so as to enable anchorage of the prosthesis at the implantation site.

2. The method of claim 1, wherein positioning the prosthesis further includes positioning the proximal portion of the armature at a location proximal to the Valsalva sinuses, and positioning the distal portion of the armature at a location distal to the Valsalva sinuses.

3. The method of claim 2, wherein radially expanding the prosthesis includes radially expanding the proximal portion so that it engages a wall of the valve annulus, and radially expanding the distal portion so that it engages a vessel wall distal to the plurality of Valsalva sinuses.

4. The method of claim 3, wherein the proximal portion has an outwardly-flared proximal end, and wherein radially expanding the proximal portion includes causing the outwardly-flared proximal end to anchor against the valve annulus.

5. The method of claim 1, wherein positioning the prosthesis at the implantation site is performed using a catheter to retain the prosthesis in the radially collapsed configuration.

6. The method of claim 1, wherein the armature is configured to be self-expandable from the radially collapsed configuration to a radially expanded configuration, and wherein radially expanding the prosthesis includes allowing the armature to self-expand toward the radially expanded configuration.

7. The method of claim 6, wherein the armature is made from a material having shape memory properties.

8. The method of claim 6, wherein allowing the armature to self-expand toward the radially expanded configuration includes disengaging the prosthesis from a sheath retaining the prosthesis in the radially collapsed configuration.

9. The method of claim 1, wherein the first, second and third Valsalva sinus anchors each include a pair of anchor members.

10. The method of claim 9, wherein positioning the prosthesis includes positioning the anchor members of each pair of anchor members on opposite sides of a coronary ostium located in one or more of the respective Valsalva sinuses.

* * * * *